US006512023B1

(12) United States Patent
Malofsky et al.

(10) Patent No.: US 6,512,023 B1
(45) Date of Patent: Jan. 28, 2003

(54) STABILIZED MONOMER ADHESIVE COMPOSITIONS

(75) Inventors: Bernard Malofsky, Bloomfield, CT (US); Andrés Rivera, Raleigh, NC (US); Gabriela Rueda, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/099,457

(22) Filed: Jun. 18, 1998

(51) Int. Cl.[7] .............................................. C09J 133/14
(52) U.S. Cl. .................... 523/111; 424/78.35; 514/527; 523/118; 523/122; 523/176; 523/177; 558/305; 558/306; 558/307; 602/48; 602/52; 602/58
(58) Field of Search ................................. 523/111, 118, 523/176, 177, 122; 514/527; 424/78.35; 602/48, 52, 58; 558/305, 306, 307

(56) References Cited

U.S. PATENT DOCUMENTS

| | | | |
|---|---|---|---|
| 2,721,858 A | 10/1955 | Joyner et al. | |
| 2,765,332 A | 10/1956 | Coover, Jr. et al. | |
| 2,768,109 A | 10/1956 | Coover, Jr. | |
| 2,784,215 A | 3/1957 | Joyner | |
| 3,254,111 A | 5/1966 | Hawkins et al. | |
| 3,360,124 A | 12/1967 | Stonehill | |
| 3,483,870 A | 12/1969 | Coover, Jr. et al. | |
| 3,527,841 A | 9/1970 | Wicker, Jr. et al. | |
| 3,554,990 A | 1/1971 | Quinn et al. | |
| 3,559,652 A | 2/1971 | Banitt et al. | |
| 3,940,362 A | 2/1976 | Overhults | |
| 3,995,641 A | 12/1976 | Kronenthal et al. | |
| 4,086,266 A | 4/1978 | Corey | |
| 4,125,494 A | 11/1978 | Schoenberg et al. | |
| 4,127,382 A | 11/1978 | Perry | |
| 4,182,823 A | * 1/1980 | Schoenberg | 526/298 |
| 4,313,865 A | 2/1982 | Teramoto et al. | |
| 4,321,180 A | 3/1982 | Kimura et al. | |
| 4,364,876 A | 12/1982 | Kimura et al. | |
| 4,440,910 A | * 4/1984 | O'Connor | 525/295 |
| 4,479,933 A | 10/1984 | Akimova et al. | |
| 4,496,685 A | * 1/1985 | Nagasawa et al. | 524/708 |
| 4,560,723 A | 12/1985 | Millet et al. | |
| 4,574,097 A | 3/1986 | Honeycutt | |
| 4,650,826 A | 3/1987 | Waniczek et al. | |
| 4,720,513 A | 1/1988 | Kameyama et al. | |
| 4,980,086 A | 12/1990 | Hiraiwa et al. | |
| 5,034,456 A | * 7/1991 | Katsumura et al. | 524/850 |
| 5,259,835 A | 11/1993 | Clark et al. | |
| 5,328,687 A | 7/1994 | Leung et al. | |
| 5,455,369 A | 10/1995 | Meier et al. | |
| 5,514,371 A | 5/1996 | Leung et al. | |
| 5,514,372 A | 5/1996 | Leung et al. | |
| 5,530,037 A | 6/1996 | McDonnell et al. | |
| 5,575,997 A | 11/1996 | Leung et al. | |
| 5,582,834 A | 12/1996 | Leung et al. | |
| 5,624,669 A | 4/1997 | Leung et al. | |
| 5,753,699 A | 5/1998 | Greff et al. | |
| 5,807,563 A | * 9/1998 | Askill et al. | 424/402 |
| 5,874,044 A | * 2/1999 | Kotzev | 422/1 |

FOREIGN PATENT DOCUMENTS

| | | |
|---|---|---|
| BE | 890553 | 3/1982 |
| DE | 3140246 | 4/1983 |
| GB | 1392400 A | 4/1975 |
| GB | 2 107 328 A | 4/1983 |
| GB | 2 306 469 A | 5/1997 |
| JP | 46-18147 | 5/1971 |
| JP | 62-100568 | 5/1987 |
| JP | 7-252455 | 10/1995 |
| WO | WO 97/31598 | 9/1997 |

OTHER PUBLICATIONS

US 6,339,259, 1/2002, Cobbley et al. (withdrawn)*
Encyclopedia of Chemical Technology, vol. 23, p. 195 John Wiley & Sons (1997).
Catalogue Merck (1999/2000) Réactifs Produits Chimiques, p. 28478.

* cited by examiner

Primary Examiner—Peter Szekely
(74) Attorney, Agent, or Firm—Oliff & Berridge, PLC

(57) ABSTRACT

An adhesive composition includes a polymerizable adhesive monomer, at least one vapor phase stabilizer, and at least one liquid phase stabilizer. The combination of at least one vapor phase stabilizer and at least one liquid phase stabilizer provides superior stabilization and shelf-life for the monomer composition. The stabilized adhesive composition provides superior performance and shelf-life and can be sterilized without significant polymerization of the monomer.

102 Claims, No Drawings

STABILIZED MONOMER ADHESIVE COMPOSITIONS

BACKGROUND OF THE INVENTION

1. Field of the Invention

The invention relates to monomer and polymer adhesive and sealant compositions, and to their production for industrial and medical uses.

2. State of the Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

Industrial production of 1,1-disubstituted ethylene adhesive compositions has been optimized to provide adhesives with rapid cure rates and high bond strengths. However, the desire to provide an adhesive with a rapid cure rate has led to problems with shelf-life. The shelf-life of these adhesives is primarily related to stability (i.e., constancy of compositional nature), uncured physical properties, rate of cure of the adhesive, as well as final cured properties of the composition. For example, the shelf-life of a monomeric a-cyanoacrylate composition is related to the amount of time the composition can be stored before unacceptable levels of polymerization occur. Unacceptable levels are indicated by a level of polymerization product that reduces the usefulness of the composition in the application for which it is produced.

It is known that monomeric forms of α-cyanoacrylates are extremely reactive, polymerizing rapidly in the presence of even minute amounts of an initiator, including moisture present in the air or on moist surfaces such as animal tissue. Monomers of α-cyanoacrylates are anionically polymerizable or free radical polymerizable, or polymerizable by zwitterions or ion pairs to form polymers. Once polymerization has been initiated, the cure rate can be very rapid. Therefore, in order to obtain a monomeric α-cyanoacrylate composition with an extended shelf-life, polymerization inhibitors such as anionic and free radical stabilizers are often added to the compositions. However, addition of such stabilizers can result in substantial retardation of the cure rate of the composition. Therefore, in the production of industrial acyanoacrylate adhesives, the amount of stabilizers added is minimized so that the cure rate is not adversely affected.

One anionic stabilizer that has been used is sulfur dioxide. Unfortunately, the use of this stabilizer, while providing stabilization, results in a loss in cure rate as the composition ages. This is because the sulfur dioxide is continuously being oxidized to sulfuric acid, which is also an anionic stabilizer. As the sulfuric acid concentration increases in the composition, the cure rate of the composition decreases. This effect is often referred to as "speed loss" and is a significant problem encountered with the production and storage of industrial α-cyanoacrylate adhesives. In extreme cases, the levels of sulfuric acid become so high that the monomer composition cannot polymerize. Additionally, the conversion of sulfur dioxide to sulfuric acid reduces the amount of sulfur dioxide in the vapor phase, which results, eventually, in the formation of polymers in the head space (vapor phase) of the container. This polymerization within the container further contributes to the loss in shelf-life of the composition.

In addition to their uses in industrial settings, 1,1-disubstituted ethylene adhesives have been used in medical applications. These applications include use as an alternate and an adjunct to surgical sutures and staples in wound closure as well as for covering and protecting surface wounds such as lacerations, abrasions, burns, stomatitis, sores, and other open surface wounds. Cyanoacrylate adhesives for use in medical applications preferably have a shelf-life of at least twelve months. In order to achieve a useful shelf-life, anionic and free-radical stabilizers are added to the monomer compositions.

As disclosed in U.S. Pat. No. 3,559,652 to Banitt et al. and U.S. Pat. No. 5,582,834 to Leung et al., for example, suitable stabilizers for medically useful α-cyanoacrylate compositions include Lewis acids such as sulfur dioxide, nitric oxide, and boron trifluoride, as well as free-radical stabilizers including hydroquinone, monomethyl ether hydroquinone, nitrohydroquinone, catechol, and monoethyl ether hydroquinone. The combination of the two anionic stabilizers sulfur dioxide and sulfonic acid is also known and is disclosed in, for example, British Patent Application GB 2 107 328 A. However, the use of these two anionic stabilizers in combination does not overcome the "speed loss" seen in other 1,1-disubstituted ethylene adhesive compositions.

In addition to having an extended shelf-life, cyanoacrylate compositions for use in medical applications should be sterile. Due to the importance of achieving and maintaining sterility of these compositions, when an additive, such as an anionic or free-radical stabilizer, is added to an α-cyanoacrylate composition, it should be added prior to sterilization. However, regardless of the type and number of additives, sterilization of α-cyanoacrylate adhesive compositions is often difficult to achieve. For example, widely practiced methods of sterilization, such as heat sterilization and ionizing radiation are often not suitable for use with monomeric cyanoacrylate compositions. Problems arise due to polymerization of the monomer during the sterilization process, even in the presence of stabilizers. In many cases, sterilization-induced polymerization is so severe that the resulting product is unusable. Furthermore, even when the sterilized product is still useable, the shelf-life at room temperature can be shortened to such a degree that the product is not suitable for commercialization.

Methods currently used to package and sterilize α-cyanoacrylate monomer compositions have been developed with the recognition that, to improve efficiency and productivity, the packaging and sterilizing steps should be performed in rapid succession. However, these methods do not provide the desired shelf-life of the adhesive compositions in all packaging materials.

Furthermore, during sterilization, much or all of the stabilizer can be consumed or converted to another compound. For example, U.S. Pat. No. 5,530,037 to McDonnell et al. discloses that when a low level of sulfur dioxide is used to stabilize a cyanoacrylate composition, all of the sulfur dioxide is converted to sulfuric acid during the sterilization process. Thus, although polymerization during sterilization can be minimized by use of low levels of sulfur dioxide, and shelf-life of the sterilized α-cyanoacrylate adhesive composition can be increased, shelf-life might be improved by the presence of increased amounts of sulfur dioxide in the initial composition. Unfortunately, at initial high levels of a stabilizer, the general performance of the adhesive can be impaired and the shelf life provided still is less than desired.

Interestingly, McDonnell et al. also teach that the use of the free radical stabilizers butylated hydroxyanisole (BHA) and butylated hydroxytoluene (BHT), in combination with 100 parts per million (final concentration) sulfur dioxide, are not effective at stabilizing acyanoacrylate compositions during gamma irradiation sterilization until they are present in concentrations substantially above 1000 parts per million or higher (see Example 4 of McDonnell et al.).

Thus, a need exists for improved monomer cyanoacrylate adhesive compositions, for both industrial and medical uses, having a longer shelf-life without sacrificing the performance of the adhesive.

SUMMARY OF THE INVENTION

The present invention provides an improved adhesive composition, as well as a method of making, and a method of sterilizing such an adhesive composition. The improved composition is achieved through the use of a novel combination of stabilizers.

The present invention provides a monomer-containing adhesive composition comprising a polymerizable α-cyanoacrylate monomer, at least one stabilizer that stabilizes the vapor state (also referred to herein as the vapor phase or gaseous phase), and at least one other stabilizing agent that stabilizes the liquid state (also referred to herein as the liquid phase). As used herein, a stabilizing agent (or stabilizer) is any substance that blocks or inhibits initiation of polymerization or terminates polymerization of a polymerizable 1,1-disubstituted ethylene monomer, or reduces the overall rate of polymerization of a composition comprising a polymerizable 1,1-disubstituted ethylene monomer. Inhibition can occur at initiation or chain elongation. In embodiments, the liquid phase stabilizer is a strong acid, preferably a very strong acid.

The combination of a polymerizable monomer with at least one gaseous phase and at least one liquid phase stabilizer according to the present invention provides an adhesive monomer composition with an enhanced and extended shelf-life as compared to similar acyanoacrylate monomer compositions lacking either or both types of stabilizers. Although it is known to add polymerization inhibitors (stabilizers) to monomeric adhesive compositions, the superiority of the use of a combination of at least one vapor phase and at least one liquid phase stabilizer according to the present invention, together in a single monomeric adhesive composition, has not previously been recognized. It has been recognized that, due to the low molecular weight of α-cyanoacrylate monomers, a portion of the monomers exist in the vapor phase. This is especially true during sterilization processes where heat is applied or generated, because the heat causes an increase in the amount of monomer in the vapor phase. Unstabilized monomers in the vapor phase can polymerize, on the walls of the container, for example. Thus, stabilization of the vapor phase as well as the liquid phase is necessary to minimize unwanted polymerization of the monomers and improve shelf-life.

The present invention also includes a process for producing such stabilized compositions. Production of these stabilized compositions includes combining the monomer with the stabilizers and can also include packaging and sterilizing the monomer-containing adhesive compositions. The compositions produced and packaged according to the present invention have longer shelf-lives, thus extended utility, as compared to α-cyanoacrylate adhesive compositions of the prior art.

The present invention further includes a method of sterilizing a monomer-containing adhesive composition that comprises at least one vapor phase and at least one liquid phase stabilizer. The monomeric composition can be sterilized without unacceptable levels of polymerization occurring. Thus, the present invention also provides a sterile monomer-containing adhesive composition that has an improved shelf-life and higher monomer to polymer ratio than compositions prepared by prior methods.

DETAILED DESCRIPTION OF PREFERRED EMBODIMENTS

According to the invention, a stable monomeric adhesive composition is manufactured by adding both at least one anionic vapor phase stabilizer and at least one anionic liquid phase stabilizer, to a composition comprising a monomer adhesive. The combination of at least one vapor phase stabilizer and at least one liquid phase stabilizer according to the present invention inhibits polymerization of the monomers of the composition to a greater extent than can be achieved by prior art compositions.

The anionic vapor phase stabilizers may be selected from among known stabilizers, including, but not limited to, sulfur dioxide, boron trifluoride, and hydrogen fluoride. The amount of anionic vapor phase stabilizer that is added to the monomer composition depends on the identity of the liquid phase stabilizer(s) chosen in combination with it, the monomer to be stabilized, as well as the packaging material to be used for the composition. A sufficient amount of anionic vapor phase stabilizer is added so that at least some of the anionic vapor phase stabilizer remains in the vapor phase after completion of the sterilization process to stabilize monomers present in the vapor phase. Preferably, each anionic vapor phase stabilizer is added to give a concentration of less than 200 parts per million (ppm). In preferred embodiments, each anionic vapor phase stabilizer is present from about 1 to 200 ppm, more preferably from about 10 to 75 ppm, even more preferably from about 10 to 50 ppm, and most preferably from 10 to 20 ppm. The amount to be used can be determined by one of ordinary skill in the art using known techniques without undue experimentation.

In embodiments, the vapor phase comprises, among other things, an anionic stabilizer that is sulfur dioxide. In embodiments, the vapor phase comprises, among other things, a stabilizer that is boron trifluoride or hydrogen fluoride. A combination of sulfur dioxide and boron trifluoride or hydrogen fluoride is preferable in some embodiments.

In embodiments, the liquid phase anionic stabilizer is a very strong acid. As used herein, a very strong acid is an acid that has an aqueous $pK_a$ of less than 1.0. Suitable very strong acidic stabilizing agents include, but are not limited to, very strong mineral and/or oxygenated acids. Examples of such very strong acids include, but are not limited to, sulfuric acid ($pK_a$ –3.0), perchloric acid ($pK_a$ –5), hydrochloric acid ($pK_a$ –7.0), hydrobromic acid ($pK_a$ –9), fluorosulfonic acid ($pK_a$ <–10), chlorosulfonic acid ($pK_a$ –10). In embodiments, the very strong acid liquid phase anionic stabilizer is added to give a final concentration of 1 to 200 ppm. Preferably, the very strong acid liquid phase anionic stabilizer is present in a concentration of from about 5 to 80 ppm, more preferably 10 to 40 ppm. The amount of very strong acid liquid phase anionic stabilizer to be used can be determined by one of ordinary skill in the art without undue experimentation.

Preferably, the very strong acid liquid phase anionic stabilizer is sulfuric acid, perchloric acid, or chlorosulfonic acid. More preferably, the very strong acid liquid phase anionic stabilizer is sulfuric acid.

In embodiments, sulfur dioxide is used as a vapor phase anionic stabilizer and sulfuric acid is used as a liquid phase anionic stabilizer.

Boron trifluoride and/or hydrogen fluoride in combination with a very strong acid liquid stabilizer may be used in some preferred embodiments. This combination is particularly useful in conjunction with plastic containers and, while applicable to all monomer adhesive compositions of the present invention, is particularly suitable for those intended for industrial uses. The use of boron trifluoride and/or hydrogen fluoride as the vapor phase anionic stabilizer avoids "speed loss" of the compositions because neither boron trifluoride nor hydrogen fluoride is oxidized to a liquid phase anionic stabilizer. The use of these vapor phase anionic stabilizers thus provides a composition with a particularly extended shelf life.

A combination of boron trifluoride and/or hydrogen fluoride with sulfur dioxide and a very strong acid anionic stabilizer is used in some preferred embodiments. For example, a combination of boron trifluoride, sulfur dioxide, and sulfuric acid may be used. This combination includes a small amount of boron trifluoride or hydrogen fluoride in conjunction with the sulfur dioxide and very strong acid anionic stabilizer. This combination can be used with many monomer adhesive compositions and packaging materials. The boron trifluoride and/or hydrogen fluoride may act to remove destabilizing materials present on the surface of the packaging material, thus removing polymerization initiators that could reduce the shelf-life of the packaged composition. The amount of boron trifluoride and/or hydrogen fluoride used should be selected to effect shelf-life improvement without causing unacceptable damage to the container. Such amounts depend on the selection and volume of the composition and container, but can be determined by those of ordinary skill in the art without undue experimentation.

In embodiments, the liquid phase anionic stabilizer is a strong acid. As used herein, a strong acid is an acid that has an aqueous $pK_a$ less than 2. Thus, strong acids include the very strong acids discussed above.

Suitable strong acids include, but are not limited to, strong mineral acids and strong organic acids. Examples of such acids include, but are not limited to, a sulfonic acid, such as methanesulfonic acid. In embodiments, the liquid phase strong acid stabilizer is added to give a final concentration of less than 200 ppm, preferably between 5 and 80 ppm, more preferably between 10 and 40 ppm. In embodiments, the strong acid liquid phase anionic stabilizer is an organic sulfonic acid.

The compositions may also optionally include at least one other anionic stabilizing agent that inhibits polymerization. These agents are herein referred to as secondary anionic active agents to contrast them with the strong or very strong liquid phase anionic stabilizers, which are referred to hereinbelow as "primary" anionic stabilizers. The secondary anionic active agents can be included in the compositions to adjust the cure speed of the adhesive composition, for example.

The secondary anionic active agent would normally be an acid with a higher $pK_a$ than the primary anionic stabilizing agent and may be provided to more precisely control the cure speed and stability of the adhesive, as well as the molecular weight of the cured adhesive. Any mixture of primary anionic stabilizers and secondary active agents is included as long as the chemistry of the composition is not compromised and the mixture does not significantly inhibit the desired polymerization of the composition. Furthermore, the mixture should not, in medical adhesive compositions, show unacceptable levels of toxicity.

Suitable secondary anionic active agents include those having aqueous $pK_a$ ionization constants ranging from 2 to 8, preferably from 2 to 6, and most preferably from 2 to 5. Examples of such suitable secondary anionic stabilizing agents include, but are not limited to, phosphoric acid ($pK_a$ 2.2), organic acids, such as acetic acid ($pK_a$ 4.8), benzoic acid ($pK_a$ 4.2), chloroacetic acid ($pK_a$ 2.9), cyanoacetic acid, and mixtures thereof. Preferably these secondary anionic stabilizing agents are organic acids, such as acetic acid or benzoic acid. In embodiments, the amount of acetic acid and/or benzoic acid is about 25–500 ppm. The concentration of acetic acid is typically 50–400 ppm, preferably 75–300 ppm, and more preferably 100–200 ppm. When using a stronger acid such as phosphoric acid, a concentration of 20–100 ppm, preferably 30–80 ppm, and more preferably 40–60 ppm may be utilized.

In embodiments where a strong acid liquid phase anionic stabilizer is the only anionic liquid phase stabilizer used, the composition will preferably comprise either boron trifluoride or hydrogen fluoride, or both, as the vapor phase anionic stabilizer. In these embodiments, the use of a combination of boron trifluoride and/or hydrogen fluoride in combination with the strong acid liquid phase anionic stabilizer improves the shelf-life of the composition (as compared to the use of sulfur dioxide as the vapor phase anionic stabilizer) by avoiding "speed loss." Because neither boron trifluoride nor hydrogen fluoride is oxidized over time to give a liquid phase stabilizer, no substantial increase in polymerization time of the monomer adhesive composition is seen as the composition ages. In such embodiments where boron trifluoride and/or hydrogen fluoride are used as the only vapor phase stabilizers, the container is preferably not glass, although there can be embodiments where these vapor phase anionic stabilizers are used in very small quantities that do not significantly affect the integrity of the glass container.

Combinations of at least one vapor phase stabilizer and at least one liquid phase anionic stabilizer are used. For example, combinations of sulfur dioxide and sulfuric acid, sulfur dioxide and perchloric acid, sulfur dioxide and chlorosulfonic acid, boron trifluoride and sulfuric acid, boron trifluoride and perchloric acid, boron trifluoride and chlorosulfonic acid, boron trifluoride and methanesulfonic acid, hydrogen fluoride and sulfuric acid, hydrogen fluoride and perchloric acid, hydrogen fluoride and chlorosulfonic acid, and hydrogen fluoride and methanesulfonic acid can be used. A combination of boron trifluoride, sulfur dioxide, and sulfuric acid can also be used, among other combinations. The two types of anionic stabilizers are chosen in conjunction such that the stabilizers are compatible with the chosen adhesive composition and each other stabilizer, as well as with the packaging material and the equipment used to make and package the composition. In other words, the combination of vapor phase stabilizer(s), liquid phase stabilizer(s), and monomer should be such that a stabilized, substantially unpolymerized adhesive composition is present after packaging.

The present invention provides an adhesive composition comprising at least one vapor phase anionic stabilizer and at least one liquid phase anionic stabilizer that are added to an adhesive composition containing at least one free radical stabilizer (also known as a free radical inhibitor or antioxidant). Although it is known to add free radical stabilizers to acyanoacrylate compositions, the advantages of a combination of at least one vapor phase anionic stabilizer, at least one liquid phase anionic stabilizer, and a free radical stabilizer has not been recognized before. The compositions of the invention show enhanced shelf-life, in the manner of the compositions according to the invention described above. Additionally, by adding at least one vapor phase anionic stabilizer and at least one liquid phase anionic stabilizer to a composition comprising a free radical stabilizer, the resulting composition can be sterilized to produce a stable, sterile composition with an enhanced shelf-life.

Compositions according to the invention can also comprise a medicament. Inclusion of a medicament is often desirable in compositions intended for medical applications. The medicament can either be added to the monomer-containing adhesive composition prior to packaging, or, alternatively, the medicament is applied to a tissue prior to application of the monomer-containing adhesive composition. The medicament can act to initiate and/or accelerate polymerization of the monomer composition in addition to serving its medicinal function.

Examples of such medicaments include, but are not limited to antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof.

Exemplary medicaments include, but are not limited to, quaternary ammonium halides such as benzalkonium chloride and benzethonium chloride; chlorhexidine sulfate; gentamicin sulfate; hydrogen peroxide; quinolone thioureas; silver salts, including, but not limited to, silver acetate, silver benzoate, silver carbonate, silver chloride, silver citrate, silver iodide, silver nitrate, and silver sulfate; sodium hypochlorite; salts of sulfadiazine, including, but not limited to silver, sodium, and zinc salts; and mixtures thereof.

Preferable medicaments are those that are anions or help in radical generation or that are ion pairs or are themselves radicals.

In embodiments, the medicament is preferably a quaternary ammonium halide such as alkylbenzyldimethylammonium chloride (benzalkonium chloride; BAC) with an alkyl containing 6–18 carbon atoms, its pure components, or mixtures thereof, or benzethonium chloride; or a salt of sulfadiazine, such as a silver, sodium, or zinc salt.

The medicament can have a pharmaceutical effect only at the site of application (i.e., limited to the tissue on/in which it is applied), or it can have a systemic effect (by systemic, it is not only meant that the medicament has an effect throughout the patient's body, but also at a specific site other than the site of application). In embodiments where the medicament is applied in an amount sufficient to show a systemic pharmaceutical activity, it can be absorbed, transported, or otherwise distributed to the site or sites within the patient where the pharmaceutical activity is desired, e.g., through the cardiovascular or lymph systems. The medicament may be in the form of a solid, such as a powder or a solid film, or in the form of a liquid, such as a watery, viscous, or paste-like material. The medicament may also be compounded with a variety of additives, such as surfactants or emulsifiers, and vehicles.

In another embodiment, the present invention is directed to a method of treating a superficial or topical pathology, including, but not limited to a skin wound such as a superficial laceration, burn, or abrasion, or a sore on a mucous membrane. The method can comprise making an adhesive composition comprising a medicament and applying this composition to a site to be treated. Alternatively, the method can comprise (a) applying a medicament (that can be a polymerization initiator or rate accelerator) to the affected tissue, (b) applying a polymerizable monomer-containing adhesive composition over the medicament; (c) allowing the composition to polymerize; and (d) optionally, applying the composition at least once more to the same site.

Suitable film thickness for such topical applications is preferably between 1 and 10,000 $\mu$m, for example between 1 and 1000 $\mu$m. In embodiments, the biocompatible film so formed may have a film strength of at least 5 mm Hg, such as 5–400 mm Hg, preferably from 50–400 mm Hg.

In embodiments, the present invention provides a method of delivering a medicament to a tissue. The method can comprise making a composition comprising a medicament, applying the composition to a site, allowing the composition to polymerize, and maintaining the polymerized composition in contact with the site for a sufficient amount of time to allow the medicament to be delivered to the target site. Alternatively, the method can comprise (a) applying a medicament (that can be a polymerization initiator and/or polymerization rate accelerator) to a site (e.g., directly to tissue); (b) applying a polymerizable monomer-containing composition over the medicament; and (c) optionally, applying the composition at least once more to the same site. Suitable film thickness and strength are preferably those disclosed above for other uses.

In embodiments, the medicament is released to the tissue to which it is in contact at a constant, or near constant, rate over a period of time while in contact with the affected tissue.

The present invention also provides a kit for providing the compositions of the invention to a user. In embodiments, the invention provides a kit for delivering a medicament to a patient. In this embodiment, the kit comprises a container with a polymerizable monomer composition, such as a cyanoacrylate adhesive. The kit also comprises another container with a medicament. Alternatively, the kit can comprise one container holding a composition comprising both the adhesive and the medicament. In embodiments, multiple containers are present in the kit, each holding one or more polymerizable monomers and one or more medicaments. Some containers can hold mixtures of adhesives and medicaments.

The medicament is selected so that it functions in conjunction with the co-packaged polymerizable monomer composition to initiate polymerization of the monomer or modify (e.g., accelerate) the rate of polymerization for the monomer to form a polymeric adhesive. The proper combination of medicament and polymerizable monomer can be determined easily by one of skill in the art. The medicament is supplied in the kit in an amount that will be pharmaceutically effective when applied topically (i.e., directly to tissue).

Compositions according to the invention can be manufactured and sterilized in very small quantities. Typically, sterilized $\alpha$-cyanoacrylate compositions must be sterilized in large volumes (e.g., 1–5 milliliters). When intended for medical applications, this large volume is undesirable because much of the composition is discarded after the first use out of fear of contamination of the composition. Thus, providing sterile $\alpha$-cyanoacrylate compositions in smaller volumes is desirable. The use of at least one vapor phase anionic stabilizer and at least one liquid phase anionic stabilizer in conjunction with a free radical stabilizer according to the present invention permits sterilization of less than 1 milliliter (ml.) of the adhesive composition. Thus, the sterilized compositions of such embodiments of the invention provide an improvement over the sterile compositions currently available.

Preferably, a composition according to the invention is packaged such that a total volume of no more than 1 ml. of the adhesive composition is present per package (i.e., container). More preferably, no more than 0.6 ml. of the adhesive composition is present. Such compositions of the invention can be sterilized by appropriate means, including, but not limited to, dry heat sterilization, gamma irradiation, microwave irradiation, and electron beam irradiation.

In embodiments, adhesive compositions according to the invention are sterilized. In embodiments where the compositions are to be used for medical applications, the sterilized composition must show low levels of toxicity to living tissue during its useable life. According to the invention, the combination of at least one vapor phase and at least one liquid phase anionic stabilizer provides sufficient inhibition of polymerization of the monomer (i.e., stabilization of the composition) that sterility can be achieved without the unacceptable levels of polymerization or increases in cure rate due to over-stabilization that result from methods disclosed in the prior art. For example, sterilized compositions according to embodiments of the present invention show an increase in viscosity of no more than 300% as a result of sterilization. Viscosity levels can be determined by known techniques. For example, viscosity can be determined at room temperature (approximately 21–25° C.) using a Brookfield Cone-Plate Viscometer with spindle size CP-40. The instrument is standardized using a Viscosity Reference Standard in the same range as the sample to be tested. Each sample is measured three times, and an average value determined and recorded.

The monomer-containing composition may be packaged in any type of suitable container fabricated from materials including, but not limited to, glass, plastic, metal packages, and film-formed packages. Suitable containers are those into which the compositions can be dispensed and sterilized without unacceptable damage to, or degradation of, the container or the components of the monomer composition. Glass is preferred especially when sterilization is achieved with dry heat because of the lack of stability of many plastics at the temperatures used for dry heat sterilization (typically at least 160° C.). Examples of types of containers include, but are not limited to, ampoules, vials, syringes, pipettes, and the like. In a preferred embodiment, the container comprises a sealable container. The container can be of any size, and in embodiments holds a total volume of no more than 1 ml. For example, the container may hold a total volume of 1 ml. and contain 0.6 ml. of the monomer composition.

To be considered sterile, the composition must show no bacterial growth after inoculation onto Soybean Casein Digest media, and incubation for 14 days at 32–35° C. Standard procedures and materials, such as those disclosed in USP XXIII <1211>, "Sterilization and Sterility Assurance of Compendial Articles" should be followed.

In preferred embodiments, a stable, sterile, substantially unpolymerized α-cyanoacrylate composition is provided in a glass ampoule. It has been found that, in order to package and sterilize an α-cyanoacrylate adhesive composition in a glass ampoule, using sulfur dioxide as the vapor phase anionic stabilizer and sulfuric acid as the liquid phase anionic stabilizer, it is particularly desirable to dispense the composition into the ampoule, seal the ampoule, then wait a pre-determined amount of time, such as one or two days or more before sterilizing. This method results in a decrease in unwanted polymerization of the composition during and/or immediately after the sterilization process. The stable, sterilized adhesive composition so obtained thus has a lower polydispersity and a higher ratio of monomer to unwanted polymerization product than can be achieved by currently used packaging and sterilization methods. Such compositions so treated have shown substantially no conversion of monomer to polymer during sterilization. Sterilization of the monomer-containing glass ampoule can be achieved using various sterilization techniques, including dry heat sterilization.

According to embodiments of the present invention, the stability, and thus the shelflife, of some adhesive compositions can be further enhanced and extended through careful regulation of the packaging (i.e., dispensing into a container) and sterilizing procedure. Contrary to the prevailing desire to minimize the time required to prepare and sterilize this type of composition, waiting a predetermined amount of time between the packaging of an adhesive composition, particularly in glass, and the sterilization of that composition may result in a decrease in unwanted polymerization products during and immediately after sterilization. The process optimizes the time between placing a liquid adhesive composition comprising a polymerizable monomer in a glass container and sterilizing it. The methods, in conjunction with the novel compositions disclosed herein, effectively minimize or eliminate undesirable levels of polymerization of the monomer, thus providing stable, sterile adhesive compositions.

The present invention thus includes a method for packaging and sterilizing monomer-containing compositions, for use in either industrial or medical applications. In embodiments, the method comprises:

A) dispensing a monomer-containing adhesive composition into a suitable container;

B) waiting a pre-determined amount of time, depending on the monomeric adhesive composition and on the material used to make the container, chosen to result in enhanced stability of the composition upon sterilization; and C) sterilizing the composition.

The dispensing step of the present invention (step A) can be accomplished by techniques known to the ordinary artisan including, but not limited to, dispensing under a vacuum or under an oxygen-containing atmosphere such as air.

The method of the invention may further comprise sealing the container. Preferably, sealing of the container is performed between steps A and B (after dispensing, but before waiting) or after step C (after sterilizing). However, sealing of the container after step B (after waiting a pre-determined amount of time) is also contemplated by the invention. If sealing of the container is to be performed after step C, care should be taken to avoid loss of sterility of the composition. Most preferably, sealing of the container is performed between steps A and B.

The pre-determined amount of time between dispensing the monomeric composition and sterilizing the composition is preferably optimized to yield a composition having, immediately after sterilization, a viscosity level no more than 15–20% higher than the level prior to sterilization. However, the acceptable viscosity can be as high as 200% higher than the level prior to sterilization. More preferably, the sterilized composition has a viscosity that is no more than 50% higher than the viscosity of the composition before sterilization. Most preferably, the composition has a viscosity that is essentially unchanged from the level prior to sterilization (i.e., less than 20% higher). The acceptable viscosity after sterilization will need to be below 200% higher than the initial value in order for the monomeric adhesive composition to be of high utility in the application for which it is intended. In general, the increase in viscosity during sterilization can be viewed as "premature" aging of the monomer-containing composition which reduces its useful shelf life, particularly when it is not stored at reduced temperature. In addition, the change in the viscosity is also an indication of a change in the reactivity of the monomeric composition which normally is not desired.

The pre-determined amount of time will depend on the monomer, the packaging material, and the combination of stabilizers. When using a glass container, preferably, the amount of time is at least 1 day (24 hours), and is typically about 2 days. The upper limit for waiting is dictated only by practicality and convenience to the user.

Without being limited to any one explanation, it is believed that waiting a pre-determined amount of time (e.g., at least one day) between dispensing and sterilizing the composition provides sufficient time for the stabilizing agents, especially the liquid phase anionic stabilizing agent, to react with and remove destabilizing materials that are present on the inside surface of the packaging material. For example, when sealing a glass container, fresh glass is made. By waiting after sealing, sufficient time is allowed for the anionic stabilizers to react with the new glass and remove alkaline materials that have been newly exposed to the composition.

The sterilization step of the present invention (step C) can be accomplished by techniques known to the skilled artisan, and is preferably accomplished by methods including, but not limited to, physical and irradiation methods. Whatever method is chosen, it must be compatible with the composition to be sterilized. Examples of physical methods include, but are not limited to, sterilization by heat. Examples of irradiation methods include, but are not limited to, gamma irradiation, electron beam irradiation, and microwave irradiation. A preferred method is heat sterilization. Most preferred is dry heat sterilization.

In embodiments, the present invention is directed to methods of packaging and sterilizing monomer-containing compositions wherein the composition comprises a medically acceptable adhesive. In preferred embodiments, there is substantially no initiation of polymerization of monomeric liquid adhesive compositions that affects the utility of the monomer or monomers caused by the sterilization process. The sterilized liquid adhesive compositions have a good shelf life and excellent stability.

The monomer composition, in embodiments, is Preferably a monomeric (including prepolymeric) adhesive composition. In embodiments, the monomer is a 1,1-disubstituted ethylene monomer, e.g., an α-cyanoacrylate. Preferred monomer compositions of the present invention, and polymers formed therefrom, are useful as tissue adhesives, sealants for Preventing bleeding or for covering open wounds, and in other absorbable and non-absorbable biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, and/or stomatitis); hernia repair; meniscus repair; and aiding repair and regrowth of living tissue. Other preferred monomer compositions of the present invention, and polymers formed therefrom, are useful in industrial and home applications, for example in bonding rubbers, plastics, wood, composites, fabrics, and other natural and synthetic materials.

Monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. No. 5,328,687 to Leung, et al., which is hereby incorporated in its entirety by reference herein.

Useful 1,1-disubstituted ethylene monomers include, but are not limited to, monomers of the formula:

$$HRC=CXY \tag{I}$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include α-cyanoacrylates, vinylidene cyanides, C$_1$–C$_4$ alkyl homologues of vinylidene cyanides, dialkyl methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are α-cyanoacrylates. These monomers are known in the art and have the formula

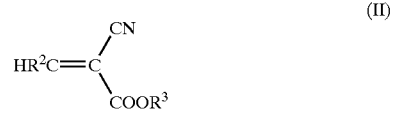

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2–4 carbon atoms, R$^5$ is an alkylene group having 2–4 carbon atoms, and R$^6$ is an alkyl group having 1–6 carbon atoms; or a group having the formula

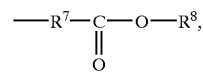

wherein R$^7$ is

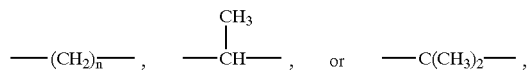

wherein n is 1–10, preferably 1–5 carbon atoms and R$^8$ is an organic moiety.

Examples of suitable hydrocarbyl and substituted hydrocarbyl groups include straight chain or branched chain alkyl groups having 1–16 carbon atoms; straight chain or branched chain C$_1$–C$_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$–$C_8$ alkyl moieties, $C_2$–$C_8$ alkenyl moieties, $C_2$–$C_8$ alkynyl moieties, $C_3$–$C_{12}$ cycloaliphatic moieties, aryl moieties such as phenyl and substituted phenyl and aralkyl moieties such as benzyl, methylbenzyl, and phenylethyl. Other organic moieties include substituted hydrocarbon moieties, such as halo (e.g., chloro-, fluoro- and bromo-substituted hydrocarbons) and oxy-substituted hydrocarbon (e.g., alkoxy substituted hydrocarbons) moieties. Preferred organic radicals are alkyl, alkenyl, and alkynyl moieties having from 1 to about 8 carbon atoms, and halo-substituted derivatives thereof. Particularly preferred are alkyl moieties of 4 to 6 carbon atoms.

In the cyanoacrylate monomer of formula (II), $R^3$ is preferably an alkyl group having 1–10 carbon atoms or a group having the formula —$AOR^9$, wherein A is a divalent straight or branched chain alkylene or oxyalkylene moiety having 2–8 carbon atoms, and $R^9$ is a straight or branched alkyl moiety having 1–8 carbon atoms.

Examples of groups represented by the formula —$AOR^9$ include 1-methoxy-2-propyl, 2-butoxy ethyl, isopropoxy ethyl, 2-methoxy ethyl, and 2-ethoxy ethyl.

The α-cyanoacrylates of formula (II) can be prepared according to methods known in the art. U.S. Pat. Nos. 2,721,858 and 3,254,111, each of which is hereby incorporated in its entirety by reference, disclose methods for preparing α-cyanoacrylates. For example, the α-cyanoacrylates can be prepared by reacting an alkyl cyanoacetate with formaldehyde in a nonaqueous organic solvent and in the presence of a basic catalyst, followed by pyrolysis of the anhydrous intermediate polymer in the presence of a polymerization inhibitor. The α-cyanoacrylate monomers prepared with low moisture content and essentially free of impurities are preferred for biomedical use.

The α-cyanoacrylates of formula (II) wherein $R^3$ is a group having the formula $R^4$—O—$R^5$—O—$R^6$ can be prepared according to the method disclosed in U.S. Pat. No. 4,364,876 to Kimura et al., which is hereby incorporated in its entirety by reference. In the Kimura et al. method, the α-cyanoacrylates are prepared by producing a cyanoacetate by esterifying cyanoacetic acid with an alcohol or by trans-esterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The α-cyanoacrylates of formula (II) wherein $R^3$ is a group having the formula

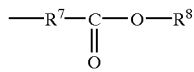

can be prepared according to the procedure described in U.S. Pat. No. 3,995,641 to Kronenthal et al., which is hereby incorporated in its entirety by reference. In the Kronenthal et al. method, such α-cyanoacrylate monomers are prepared by reacting an alkyl ester of an α-cyanoacrylic acid with a cyclic 1,3-diene to form a Diels-Alder adduct which is then subjected to alkaline hydrolysis followed by acidification to form the corresponding α-cyanoacrylic acid adduct. The α-cyanoacrylic acid adduct is preferably esterified by an alkyl bromoacetate to yield the corresponding carbalkoxymethyl α-cyanoacrylate adduct. Alternatively, the α-cyanoacrylic acid adduct may be converted to the α-cyanoacrylyl halide adduct by reaction with thionyl chloride. The α-cyanoacrylyl halide adduct is then reacted with an alkyl hydroxyacetate or a methyl substituted alkyl hydroxyacetate to yield the corresponding carbalkoxymethyl α-cyanoacrylate adduct or carbalkoxy alkyl α-cyanoacrylate adduct, respectively. The cyclic 1,3-diene blocking group is finally removed and the carbalkoxy methyl α-cyanoacrylate adduct or the carbalkoxy alkyl α-cyanoacrylate adduct is converted into the corresponding carbalkoxy alkyl α-cyanoacrylate by heating the adduct in the presence of a slight deficit of maleic anhydride.

Examples of monomers of formula (II) include cyanopentadienoates and α-cyanoacrylates of the formula:

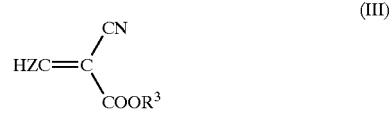

wherein Z is —CH═$CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated in its entirety by reference.

Preferred α-cyanoacrylate monomers used in this invention are alkyl α-cyanoacrylates including octyl cyanoacrylate, such as 2-octyl cyanoacrylate; dodecyl cyanoacrylate; 2-ethylhexyl cyanoacrylate; methoxyethyl cyanoacrylate; 2-ethoxyethyl cyanoacrylate; butyl cyanoacrylate such as n-butyl cyanoacrylate; ethyl cyanoacrylate; methyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. More preferred monomers are ethyl, n-butyl, and 2-octyl α-cyanoacrylate. Monomers utilized for medical purposes in the present application should be very pure and contain few impurities (e.g., surgical grade). Monomers utilized for industrial purposes need not be as pure.

The composition may also optionally include additives, such as plasticizing agents, thixotropic agents, natural or synthetic rubbers, etc. Such additives are well known to those skilled in the art. Generally, when such additives are included in adhesive compositions, the composition is destabilized, showing, for example, a lessening in shelf-life or adverse effects on the cure rate. However, the compositions of the present invention do not show the levels of such adverse effects seen in the prior art when these known additives are included. Thus, the present invention provides an improvement over the compositions presently available.

The composition may optionally include at least one plasticizing agent that imparts flexibility to the polymer formed from the monomer. The plasticizing agent preferably contains little or no moisture and should not significantly affect the stability or polymerization of the monomer. Such plasticizers are useful in polymerized compositions to be used for closure or covering of wounds, incisions, abrasions, sores or other applications where flexibility of the adhesive is desirable.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts up to 60 weight %, preferably up to 50 weight %, more preferably up to 30 weight %, and most preferably up to 10 weight % provides increased film strength (e.g., toughness) of the polymerized monomer over polymerized monomers not having plasticizing agents.

The composition may also optionally include at least one thixotropic agent. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The compositions of the invention comprise at least one radical stabilizing agent. Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole (BHA), butylated hydroxy toluene (BHT), t-butyl hydroquinone, and mixtures thereof. In embodiments, the amount of agents such as BHA is about 1,000–5,000 ppm.

Medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitrites; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium, and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines, and hydrazide.

Suitable proteins include collagen, gelatin, casein, soybean protein, vegetable protein, and keratin. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate, or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 to Perry, which is hereby incorporated in its entirety by reference. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A preferred formaldehyde scavenger for use in this invention is sodium bisulfite.

In practicing the present invention, the formaldehyde concentration reducing agent is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form. When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such bioerosion can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and deltavalerolactone, copolymers of epsilon-caprolactone and DL-dilactide, and polyester hydrogels; polyvinylpyrrolidone; polyamides; gelatin; albumin; proteins; collagen; poly(orthoesters); poly(anhydrides); poly(alkyl-2-cyanoacrylates); poly(dihydropyrans); poly(acetals); poly(phosphazenes); poly(urethanes); poly(dioxinones); cellulose; and starches.

Examples of surfactants which can be added to the mineral oil include those commercially available under the designations Triton X-100™ (Rohm and Haas), Tween 20™ (ICI Americas), and Tween 80™ (ICI Americas).

The composition may also optionally include at least one thickening agent. Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such crosslinking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or rate modifier may be added to initiate polymerization or to modify the rate of polymerization of the cyanoacrylate monomer/crosslinking agent blend.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenylamino]-9,10 anthracenedione (D+C violet No. 2); disodium salt of 6-hydroxy-5-[(4-sulfophenyl)axo]-2-naphthalenesulfonic acid (FD+C Yellow No. 6); 9-(o-carboxyphenOyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Other compositions and additives contemplated by the present invention are exemplified by U.S. Pat. Nos. 5,624,669; 5,582,834; 5,575,997; 5,514,371; 5,514,372; and 5,259,835; and U.S. patent application Ser. No. 08/714,288, the disclosures of all of which are hereby incorporated in their entirety by reference.

EXAMPLES

Example 1

Packaging and sterilizing a 2-octyl cyanoacrylate composition of the prior art in a glass container. The effect of waiting a pre-determined amount of time before sterilizing a 2-octyl cyanoacrylate adhesive composition comprising sulfur dioxide as the only anionic stabilizing agent is shown in Table 1. The data presented in Table 1 were generated as follows. A composition comprising 2-octyl cyanoacrylate, between 20 and 40 ppm sulfur dioxide, 1500 ppm hydroxyquinoline and 145 ppm paramethoxyphenol, and 150 ppm acetic acid, is prepared. One-half milliliter (0.5 ml.) of the composition is dispensed into a glass vial (ampoule). The open end of the vial is heated to the point at which the glass flows, and sealed. The sealed vial is allowed to sit at room temperature (21–25° C.) for a pre-determined amount of time (e.g., 2 or 120 hours). The temperature is not critical; however, excessive heat should not be supplied to the vial during this period. The sealed vial is then sterilized with dry heat for 1 hour at 160° C. The resulting sterilized composition is allowed to cool to room temperature.

The sterilized 2-octyl cyanoacrylate composition is removed from the vial and tested for viscosity according to the method disclosed hereinabove.

Fourteen different preparations of the same 2-octyl cyanoacrylate composition were prepared and treated in this manner. Samples of each preparation were allowed to sit for 2 hours or 120 hours between dispensing and sterilizing. The viscosity levels, in centipoise, of the fourteen samples, both before and after sterilizing, are presented in Table 1.

Table 1 shows that 2-octyl cyanoacrylate compositions stabilized with sulfur dioxide as the only anionic stabilizer show levels of viscosity, even after waiting 120 hours between dispensing and sterilizing, that are at least 122% of the levels of the unsterilized composition, and are, on average, approximately 170% of the levels of the unsterilized composition.

Example 2

Effect of waiting a pre-determined amount of time on viscosity of a composition according to the present invention. A 2-octyl cyanoacrylate composition comprising 17.5 ppm sulfuric acid (liquid phase anionic stabilizer), 15 ppm sulfur dioxide (vapor phase anionic stabilizer), 1500 ppm hydroxyquinoline and 145 ppm paramethoxyphenol (free radical stabilizers), and 150 ppm acetic acid, was dispensed into a glass ampoule, the ampoule was sealed, and the sealed adhesive composition was allowed to sit at room temperature for the indicated amount of time before sterilization by dry heat. Viscosity was determined according to the method disclosed hereinabove.

Table 2 shows the results of this experiment. Table 2 indicates that waiting a pre-determined amount of time prior to sterilizing a composition according to the present invention results in a decrease in viscosity as compared to sterilizing the composition immediately after dispensing and sealing the glass vial.

Furthermore, in contrast to the results obtained in Table 1, the composition of the present invention shows a level of viscosity that is, at most, only 113% of the level of the unsterilized composition after only 46 hours of waiting prior to sterilization. On average, these compositions showed, after sterilization, a viscosity level only 107% of the level prior to sterilization. Thus, the compositions of the present invention show greater stability as compared to compositions of the prior art.

Example 3

Stabilization of sterilized cyanoacrylate compositions. 2-octyl cyanoacrylate compositions comprising the indicated amounts of sulfur dioxide (vapor phase anionic stabilizer) and sulfuric acid (liquid phase strong acid anionic stabilizer) were prepared (containing 1500 ppm hydroxyquinoline and 145 ppm paramethoxyphenol as free radical stabilizers and 150 ppm acetic acid as secondary anionic active agent), dispensed into glass ampoules which were then sealed, and maintained at room temperature for two days. The packaged compositions were then sterilized at 160° C. for 1 hour with dry heat. The samples were then allowed to cool and the viscosity of the composition from one vial of each sample was determined as in Examples 1 and 2.

Another vial of each composition was subjected to heat at 80° C. for 12 days. Such a treatment reasonably simulates the effects on the composition of storage at ambient temperatures for 2 years.

The results of this experiment are shown in Table 3. The results show that 2-octyl cyanoacrylate compositions comprising at least 5 ppm sulfuric acid in combination with sulfur dioxide as the vapor phase anionic stabilizer show little or no increase in viscosity during or immediately after dry heat sterilization. These compositions also show remarkable stability over extended periods of time.

While the invention has been described with reference to preferred embodiments, the invention is not limited to the specific examples given, and other embodiments and modifications can be made by those skilled in the art without departing from the spirit and scope of the invention.

TABLE 1

VISCOSITY (cps)

| Sample # | Initial | T = 2 hours | T = 120 hours | % of Initial Viscosity (at 120 hours) | [$SO_2$] |
|---|---|---|---|---|---|
| 1 | 5.7 | 11 | 17 | 298 | 21 |
| 2 | 5.9 | 12 | 7.2 | 122 | 29 |
| 3 | 5.7 | 20 | 10 | 175 | 27 |
| 4 | 6.1 | 15 | 8.3 | 136 | 24 |
| 5 | 6.7 | 12 | 8.9 | 133 | 36 |
| 6 | 6.0 | 31 | 8.8 | 147 | 29 |
| 7 | 6.3 | 14 | 9.5 | 151 | 37 |
| 8 | 5.9 | 32 | 15 | 254 | 21 |
| 9 | 5.7 | 13 | 7.3 | 128 | 37 |
| 10 | 6.2 | 18 | 8.9 | 143 | 39 |
| 11 | 6.1 | 20 | 15 | 246 | 20 |
| 12 | 6.5 | 20 | 12 | 185 | 36 |
| 13 | 6.3 | 10 | 8.3 | 132 | 40 |
| 14 | 6.0 | 10 | 8 | 133 | 35 |
| Avg | 6.1 | 17 | 10.3 | 169 | 31 |

TABLE 2

Viscosity After Sterilization At 1 Hour At 160° C.*

| Batch | Length Of Lagering (hours) | Viscosity (Initial) | Viscosity (after sterilization) | % of Initial |
|---|---|---|---|---|
| 1 | 0 | 6.2 | 9.4 | 152 |
| 1 | 22 | 6.2 | 7.0 | 113 |
| 1 | 46 | 6.2 | 7.0 | 113 |
| 2 | 0 | 6.3 | 6.8 | 108 |
| 2 | 22 | 6.3 | 6.5 | 103 |
| 2 | 46 | 6.3 | 6.6 | 105 |
| 3 | 0 | 6.2 | 7.6 | 122 |
| 3 | 22 | 6.2 | 7.2 | 116 |
| 3 | 46 | 6.2 | 6.8 | 110 |
| 4 | 0 | 6.4 | 7.8 | 122 |
| 4 | 22 | 6.4 | 6.8 | 106 |
| 4 | 46 | 6.4 | 6.4 | 100 |

*17.5 ppm Sulfuric Acid; 15 ppm Sulfur Dioxide
**160° C. Dry Heat

TABLE 3

Viscosity After Sterilization At 1 Hour At 160° C.

| Sample | Sulfuric Acid (ppm) | $SO_2$ (ppm) | Viscosity* Initial | Viscosity* After Sterilization | % of Initial | Viscosity* 12 Days 80° C. |
|---|---|---|---|---|---|---|
| 1 | 15 | 1 | 6.8 | 7.1 | 104 | 9 |
| 2a | 5 | 5 | 6.9 | 8.6 | 125 | 22 |
| 2b | 5 | 5 | 6.8 | 9.4 | 138 | 28 |
| 3 | 25 | 5 | 6.6 | 6.7 | 101 | 10 |
| 4 | 1 | 15 | 6.8 | 17 | 250 | 77 |
| 5 | 0 | 50 | 6.9 | 10 | 145 | 15 |
| 6a | 15 | 15 | 6.9 | 6.9 | 100 | 11 |
| 6b | 15 | 15 | 6.7 | 7.2 | 107 | 9 |
| 6c | 15 | 15 | 6.7 | 6.9 | 103 | 9 |
| 6d | 15 | 15 | 6.6 | 7.3 | 110 | 9 |
| 6e | 15 | 15 | 6.6 | 6.9 | 104 | 9 |
| 7 | 25 | 25 | 6.7 | 6.9 | 103 | 9 |
| 8 | 15 | 29 | 6.6 | 6.9 | 104 | 8 |

*in centipoise (cps)

What is claimed is:

1. A polymerizable monomeric adhesive composition comprising a polymerizable 1,1-disubstituted ethylene monomer in a liquid phase and in a vapor phase, at least one vapor phase anionic stabilizer, and at least one liquid phase anionic stabilizer, wherein said at least one liquid phase anionic stabilizer is a very strong mineral acid.

2. The composition of claim 1, wherein said monomer is at least one member selected from the group consisting of n-butyl cyanoacrylate, 2-octyl cyanoacrylate, ethyl cyanoacrylate, methyl cyanoacrylate, ethoxyethyl cyanoacrylate, and methoxyethyl cyanoacrylate.

3. The composition of claim 1, wherein said at least one vapor phase anionic stabilizer is at least one member selected from the group consisting of sulfur dioxide, boron trifluoride, and hydrogen fluoride.

4. The composition of claim 3, wherein said at least one vapor phase anionic stabilizer comprises sulfur dioxide.

5. The composition of claim 4, wherein said sulfur dioxide is present in said composition in a concentration of 1–200 parts per million.

6. The composition of claim 5, wherein said sulfur dioxide is present in said composition in a concentration of 10–20 part per million.

7. The composition of claim 3, wherein said vapor phase anionic stabilizer comprises boron trifluoride.

8. The composition of claim 1, wherein said at least one liquid phase anionic stabilizer is at least one member selected from the group consisting of sulfuric acid, perchloric acid, fluorosulfonic acid, and chlorosulfonic acid.

9. The composition of claim 8, wherein said at least one liquid phase anionic stabilizer comprises sulfuric acid.

10. The composition of claim 9, wherein said sulfuric acid is present in said composition in a concentration of 1–200 parts per million.

11. The composition of claim 10, wherein said sulfuric acid is present in said composition in a concentration of 10–40 parts per million.

12. The composition of claim 9, wherein said composition further comprises at least one member selected from the group consisting of boron trifluoride and hydrogen fluoride.

13. The composition of claim 12, wherein said composition comprises boron trifluoride.

14. The composition of claim 1, wherein said at least one vapor phase anionic stabilizer comprises sulfur dioxide and said at least one liquid phase anionic stabilizer comprises sulfuric acid.

15. The composition of claim 14, wherein said composition is unsterilized.

16. The composition of claim 14, wherein said composition is sterilized.

17. The composition of claim 14, wherein said composition further comprises a secondary anionic agent.

18. A container containing the composition of claim 1.

19. The container of claim 18, wherein said container is made from at least one material selected from the group consisting of glass, plastic, and metal.

20. The composition of claim 1, further comprising a secondary anionic active agent.

21. The composition of claim 20, wherein the secondary anionic active agent is selected from the group consisting of phosphoric acid, acetic acid, benzoic acid, chloroacetic acid, and cyanoacetic acid.

22. The composition of claim 1, further comprising at least one medicament.

23. A method of making a sterile polymerizable 1,1-disubstituted monomer adhesive composition, comprising:
dispensing the composition of claim 1 into a container,
sealing said container, and
sterilizing the composition and the container.

24. The method of claim 23, wherein said sterilizing is by dry heat, gamma irradiation, electron beam irradiation, or microwave irradiation.

25. The method of claim 24, wherein said sterilizing is by dry heat.

26. The method of claim 24, wherein said sterilizing is by gamma irradiation.

27. The method of claim 23, wherein the sterilized composition has a viscosity less than 300% of the viscosity prior to sterilizing.

28. The method of claim 27, wherein the sterilized composition has a viscosity less than 150% of the viscosity prior to sterilizing.

29. The method of claim 23, further comprising waiting a pre-determined amount of time, which is sufficient to inhibit or eliminate polymerization of the monomer during or immediately after sterilization, before, sterilizing the dispensed composition.

30. The method of claim 29, wherein said container is made of glass, and in the sterilized composition, said at least one vapor phase anionic stabilizer comprises sulfur dioxide, and said at least one liquid phase anionic stabilizer comprises sulfuric acid.

31. The method of claim 30, wherein the sterilized composition has a viscosity that is less than 300% of said composition before sterilizing.

32. The method of claim 31, wherein the sterilized composition has a viscosity that is less than 150% of said composition before sterilizing.

33. The method of claim 29, wherein said pre-determined amount of time is at least 24 hours.

34. The method of claim 29, wherein said pre-determined amount of time is about 2 days.

35. The method of claim 23, wherein said composition has a total volume of less than 1 milliliter.

36. The method of claim 23, wherein said composition has a total volume of about 0.6 milliliter.

37. A sterile adhesive composition made by the method of claim 23.

38. A sterile adhesive composition made by the method of claim 29.

39. A sterile adhesive composition made by the method of claim 32.

40. A polymerized composition made from the composition of claim 1.

41. A polymerized composition made from the composition of claim 37.

42. A polymerized composition made from the composition of claim 38.

43. A polymerized composition made from the composition of claim 39.

44. A method of making the composition of claim 22 comprising:
combining at least one polymerizable 1,1-disubstituted ethylene monomer, at least one vapor phase anionic stabilizer, at least one liquid phase anionic stabilizer, and at least one medicament to make a composition,
wherein said at least one liquid phase anionic stabilizer is a very strong mineral acid.

45. A method of making a sterile polymerizable 1,1-disubstituted monomer adhesive composition comprising at least one medicament, comprising:
dispensing the composition of claim 44 into a container,
sealing said container, and
sterilizing the composition and the container.

46. The composition made by the method of claim 45.

47. A kit comprising the composition of claim 46.

48. A kit comprising at least one container holding at least one polymerizable 1,1-disubstituted monomer adhesive composition and at least one container holding at least one medicament, whereby said medicament is separate from said adhesive composition.

49. A method of treating a wound comprising:
applying the composition of claim 1 to a wound, and
allowing the composition to polymerize.

50. A method of treating a wound comprising:
applying the composition of claim 22 to a wound, and
allowing the composition to polymerize.

51. A method of treating a wound, comprising:
applying the composition of claim 46 to a wound, and
allowing the composition to polymerize.

52. A method of treating a wound, comprising:
applying at least one medicament to a wound surface, and
applying the composition of claim 1 over said at least one medicament to form an adhesive composition, thus treating the wound.

53. A polymerizable monomeric adhesive composition comprising a polymerizable 1,1-disubstituted ethylene monomer in a liquid phase and in a vapor phase, at least one vapor phase anionic stabilizer, at least one liquid phase anionic stabilizer, and at least one free radical stabilizer,
wherein said at least one liquid phase anionic stabilizer is a very strong mineral acid.

54. The composition of claim 53, wherein said at least one free radical stabilizer is selected from the group consisting of butylated hydroxyanisole and butylated hydroxytoluene.

55. The composition of claim 53, wherein said composition is unsterilized.

56. The composition of claim 53, wherein said composition is sterilized.

57. A method of making a sterile polymerizable 1,1-disubstituted monomer adhesive composition, comprising:
dispensing the composition of claim 53 into a container,
sealing said container, and
sterilizing the composition and the container.

58. The method of claim 57, wherein said free radical stabilizer is selected from the group consisting of butylated hydroxyanisole and butylated hydroxytoluene.

59. A polymerized composition made from the composition of claim 53.

60. A polymerizable monomeric adhesive composition comprising a polymerizable 1,1-disubstituted ethylene monomer in a liquid phase and in a vapor phase, at least one vapor phase anionic stabilizer, and at least one liquid phase anionic stabilizer,
wherein said at least one liquid phase anionic stabilizer is a strong acid mineral and wherein said at least one vapor phase anionic stabilizer is at least one member selected from the group consisting of boron trifluoride and hydrogen fluoride.

61. The composition of claim 60, wherein said monomer is at least one member selected from the group consisting of n-butyl cyanoacrylate, 2-octyl cyanoacrylate, ethyl cyanoacrylate, methyl cyanoacrylate, ethoxyethyl cyanoacrylate, and methoxyethyl cyanoacrylate.

62. The composition of claim 60, wherein said at least one vapor phase anionic stabilizer comprises boron trifluoride.

63. The composition of claim 60, wherein said at least one liquid phase anionic stabilizer comprises an organic sulfonic acid.

64. The composition of claim 63, wherein said sulfonic acid is present in said composition in a concentration of 1–200 parts per million.

65. The composition of claim 60, wherein said at least one vapor phase anionic stabilizer comprises boron trifluoride and said at least one liquid phase anionic stabilizer comprises a sulfonic acid.

66. A container containing the composition of claim 60.

67. The container of claim 66, wherein said container is made from at least one material selected from the group consisting of glass, plastic, and metal.

68. The container of claim 67, wherein said container is made from plastic.

69. The composition of claim 60, further comprising a secondary anionic active agent.

70. The composition of claim 69, wherein the secondary anionic active agent is selected from the group consisting of phosphoric acid, acetic acid, benzoic acid, chloroacetic acid, and cyanoacetic acid.

71. The composition of claim 60, further comprising at least one medicament.

72. A method of making a sterile polymerizable α-cyanoacrylate monomer adhesive composition, comprising:
dispensing the composition of claim 60 into a container,
sealing said container, and
sterilizing the composition and the container.

73. The method of claim 72, wherein said sterilizing is by dry heat, gamma irradiation, electron beam irradiation, or microwave irradiation.

74. The method of claim 73, wherein said sterilizing is by dry heat.

75. The method of claim 73, wherein said sterilizing is by gamma irradiation.

76. The method of claim 72, wherein the sterilized composition has a viscosity less than 300% of the viscosity before sterilizing.

77. The method of claim 76, wherein the sterilized composition has a viscosity less than 150% of the viscosity before sterilizing.

78. The method of claim 72, wherein said composition has a total volume of less than 1 milliliter.

79. The method of claim 72, wherein said composition has a total volume of about 0.6 milliliter.

80. A sterile adhesive composition made by the method of claim 72.

81. A sterile adhesive composition made by the method of claim 77.

82. A polymerized composition made from the composition of claim 60.

83. A polymerized composition made from the composition of claim 69.

84. A polymerized composition made from the composition of claim 71.

85. The method of claim 72, wherein the composition further comprises a secondary anionic active agent.

86. The method of claim 85, wherein the secondary anionic active agent is selected from the group consisting of phosphoric acid, acetic acid, benzoic acid, chloroacetic acid, and cyanoacetic acid.

87. A sterile composition made by the method of claim 86.

88. A polymerizable monomeric adhesive composition comprising a polymerizable 1,1-disubstituted ethylene monomer in a liquid phase and in a vapor phase, at least one vapor phase anionic stabilizer, at least one liquid phase anionic stabilizer, and at least one free radical stabilizer,
wherein said at least one liquid phase anionic stabilizer is a very strong mineral acid and wherein said at least one vapor phase anionic stabilizer is at least one member selected from the group consisting of boron trifluoride and hydrogen fluoride.

89. The adhesive composition of claim 88, wherein said at least one free radical stabilizer is selected from the group consisting of butylated hydroxyanisole and butylated hydroxytoluene.

90. A method of making an adhesive composition comprising:
combining a pre-formed polymerizable monomer with at least one vapor phase anionic stabilizer, at least one liquid phase anionic stabilizer wherein said liquid phase anionic stabilizer is a very strong mineral acid, and at least one free radical stabilizer to form said adhesive composition.

91. A method of making a sterile polymerizable 1,1-disubstituted monomer adhesive composition comprising at least one medicament, comprising:
dispensing the composition of claim 71 into a container,
sealing said container, and
sterilizing the composition and the container.

92. The composition made by the method of claim 91.

93. A kit comprising the composition of claim 92.

94. A method of treating a wound comprising:
applying the composition of claim 60 to a wound, and allowing the composition to polymerize.

95. A method of treating a wound comprising:
applying the composition of claim 69 to a wound, and allowing the composition to polymerize.

96. A method of treating a wound, comprising:

applying the composition of claim 72 to a wound, and allowing the composition to polymerize.

97. A method of treating a wound, comprising:

applying at least one medicament to a wound surface, and applying the composition of claim 60 over said at least one medicament to form an adhesive composition, thus treating the wound.

98. The kit of claim 48, wherein said at least one polymerizable 1,1-disubstituted monomer adhesive composition comprises a polymerizable monomeric adhesive composition comprising a polymerizable 1,1-disubstituted ethylene monomer in a liquid phase and in a vapor phase, at least one vapor phase anionic stabilizer, and at least one liquid phase anionic stabilizer, wherein said at least one liquid phase anionic stabilizer is a very strong mineral acid.

99. The kit of claim 48, wherein said at least one polymerizable 1,1-disubstituted monomer adhesive composition comprises a polymerizable monomeric adhesive composition comprising a polymerizable 1,1-disubstituted ethylene monomer in a liquid phase and in a vapor phase, at least one vapor phase anionic stabilizer, and at least one liquid phase anionic stabilizer, wherein said at least one liquid phase anionic stabilizer is a strong acid and wherein said at least one vapor phase anionic stabilizer is at least one member selected from the group consisting of boron trifluoride and hydrogen fluoride.

100. A method of making a polymerizable monomeric adhesive composition, comprising:

dispensing the composition of claim 1 into a container, and sealing said container.

101. A method of making a polymerizable monomeric adhesive composition, comprising:

dispensing the composition of claim 60 into a container, and sealing said container.

102. The composition of claim 1, wherein said at least one vapor phase anionic stabilizer comprises sulfur dioxide and is present in said composition in a concentration of 1–200 parts per million, and said at least one liquid phase anionic stabilizer comprises sulfuric acid and is present in said composition in a concentration of 1–200 parts per million.

* * * * *